United States Patent [19]
Phan

[11] Patent Number: 5,936,118
[45] Date of Patent: Aug. 10, 1999

[54] PROCESS FOR CHIRAL ENRICHMENT OF OPTICALLY ACTIVE CARBOXYLIC ACIDS OR SALTS OR ESTERS THEREOF

[75] Inventor: Hao V. Phan, Columbia, S.C.

[73] Assignee: Albemarle Corporation, Richmond, Va.

[21] Appl. No.: 08/833,112

[22] Filed: Apr. 4, 1997

[51] Int. Cl.$^6$ .................................................. C07B 55/00
[52] U.S. Cl. .......................................... 562/401; 560/56
[58] Field of Search ............................... 562/401; 560/56, 560/105

[56] References Cited

U.S. PATENT DOCUMENTS

| | | | |
|---|---|---|---|
| 4,246,164 | 1/1981 | Felder et al. | 562/466 |
| 4,621,152 | 11/1986 | Bernini | 562/401 |
| 4,625,054 | 11/1986 | Bernini | 562/401 |
| 5,621,140 | 4/1997 | Schloemer et al. | 562/401 |

FOREIGN PATENT DOCUMENTS

| | | |
|---|---|---|
| 0095901 | 12/1983 | European Pat. Off. . |
| 0132854 | 2/1985 | European Pat. Off. . |
| 0182279 | 5/1986 | European Pat. Off. . |

*Primary Examiner*—Samuel Barts
*Attorney, Agent, or Firm*—Philip M. Pippenger

[57] ABSTRACT

A highly efficient method for enriching the chiral purity of a partially enriched mixture of enantiomers of an optically active compound, a major portion of the partially enriched mixture of enantiomers comprising a first enantiomer of the optically active compound, a minor portion of the partially enriched mixture of enantiomers comprising a second enantiomer of the optically active compound. The method comprises mixing an acid in whatever form it may exist in solution with an aqueous solution of the partially enriched mixture of enantiomers, in whatever form the partially enriched mixture of enantiomers may exist in solution, to form a reaction mass comprising a further enriched mixture of enantiomers of the optically active compound, the further enriched mixture of enantiomers having a higher percentage of the first enantiomer than the partially enriched mixture. The optically active compound has the formula:

$$R^1R^2R^3CCOOZ$$

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl groups, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is an alkali metal cation, a cation of a nitrogenous base or a combination of the foregoing.

35 Claims, No Drawings

PROCESS FOR CHIRAL ENRICHMENT OF OPTICALLY ACTIVE CARBOXYLIC ACIDS OR SALTS OR ESTERS THEREOF

TECHNICAL FIELD

This invention relates to processes for enriching an enantiomeric mixture of an optically active carboxylic acid, or salts or esters thereof, in a desired enantiomeric form.

BACKGROUND

Profen-types of compounds are typically defined as propionic acids (or esters) bearing at least one aromatic substituent, usually α- to the carboxylic function. These acids have an asymmetric carbon atom (the carbon atom adjacent to the carbonyl group) that typically produces a racemic mixture of these acids, i.e., a mixture of both the (+) and (−) or dextro and levo rotary forms. For example, ibuprofen (2-(4-isobutylphenyl)propionic acid), a commercially and pharmaceutically important chemical, is typically produced and sold as the racemic mixture. Other profen drugs are also produced as racemates and administered in this form. However, it is known that the physiological utility of the racemic mixtures is almost exclusively focused on one enantiomer, the other having either no effect or even diminishing the effect of the active enantiomer. Thus the S(+) form of ibuprofen is active in reducing inflammation and in providing an analgesic effect. See, for example, U.S. Pat. Nos. 4,851,444 and 4,877,620. The R(−) enantiomer is devoid of activity for these indications, although it is, in part, converted in vivo into the S(+) compound. Other profen pharmaceuticals, e.g., 2-(6-methoxy-2-naphthyl)propionic acid (Naproxen), are only prescribed as the single enantiomer.

Certain commercial applications of Profen-type compounds require enantiomeric mixtures of such compounds to have chiral purity in excess of 99%. Some examples of known methods for the chiral resolution of 2-(6-methoxy-2-naphthyl)propionic acid are described in U.S. Pat. Nos. 4,625,054 and 4,621,152 to Bernini, and 4,246,164 to Felder et al. However, the known processes for the production of these types of compounds having enriched chiral purity can be laborious, complex, or otherwise inefficient in commercial practice.

A welcome contribution to the art would be a highly efficient and economical process whereby partially enriched (i.e., chiral purity in the range of greater than 50% and less than 99%) stocks of these carboxylic acids may be further enriched to thereby produce enantiomeric mixtures of such compounds having high (preferably at least 99%) chiral purity. This invention is deemed to constitute such a contribution.

SUMMARY OF THE INVENTION

This invention provides a new, economical and highly effective method for enriching the chiral purity of a partially enriched mixture (i.e., a mixture which has a chiral purity in the range of greater than 50% and less than 99%) of enantiomers of an optically active compound, a major portion (i.e., a portion in the range of more than 50% but less than 99%) of the partially enriched mixture of enantiomers comprising a first enantiomer of the optically active compound, and a minor portion (i.e., a portion in the range of greater than 0 but less than 50%) of the partially enriched mixture of enantiomers comprising a second enantiomer of the optically active compound. The optically active compound has the formula:

$$R^1R^2R^3RCCOOZ \qquad (I)$$

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl groups, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is an alkali metal cation, a cation of a nitrogenous base or a combination of the foregoing. In one embodiment, the method of this invention comprises mixing an acid in whatever form it may exist in solution with an aqueous solution of the partially enriched mixture of enantiomers, in whatever form the partially enriched mixture of enantiomers may exist in solution, to form a reaction mass comprising a further enriched mixture of enantiomers of the optically active compound, the further enriched mixture of enantiomers having a higher percentage of the first enantiomer than the partially enriched mixture. In a preferred embodiment, the optically active compound is one or more salts of 2-(6-methoxy-2-naphthyl)propionic acid (more preferably 2-(6-methoxy-2-naphthyl)propionic acid sodium salt), the major portion is in the range of more than 82% and less than 99%, and the first enantiomer is the S(+) enantiomer. The process of this invention is applicable to chiral enrichment of any original mixture of enantiomers of the optically active compounds corresponding to the above formula (I), so long as the original mixture is partially enriched in a particular enantiomer.

In another embodiment of this invention, the partially enriched mixture of enantiomers and/or the aqueous solution thereof are themselves formed by a process which comprises (i) mixing (A) a base comprising an alkali metal hydroxide or a nitrogenous compound, and (B) water, or (C) an aqueous solution formed from (A) and (B), with an organic solution of a partially enriched precursor mixture of enantiomers of a precursor optically active compound, in whatever form the partially enriched precursor mixture may exist in solution, the precursor optically active compound being of the formula as set forth in formula (I) above, with the modification that Z is a hydrogen atom, a hydrocarbyl group, or a combination of two or more of the foregoing, and (ii) separating and recovering at least a portion of an aqueous phase of the resulting solution. Preferably, the ratio of acid used in the process to optically active compound present in the aqueous solution of the partially enriched mixture of enantiomers is less than one equivalent of acid per equivalent of optically active compound. Excess or "free" base (i.e., alkali metal hydroxide or nitrogenous compound in excess of the amount of alkali metal hydroxide or nitrogenous compound theoretically consumed in forming the partially enriched mixture of enantiomers of the optically active compound) also may be present in this process. In such case, the acid may first react with such excess base before reacting with the optically active compound. Therefore, it should be understood that throughout this Specification and the appended claims the above acid to base ratio refers to the amount of acid and the amount of optically active compound which are present exclusive of the amount of acid required to react with any "free" base, if present.

This invention also provides a method for enriching the chiral purity of an enantiomeric mixture of 2-(6-methoxy-2-naphthyl)propionic acid, hydrolyzable ester thereof, or combination of the foregoing, which method comprises (i) mixing an aqueous solution of a base comprising an alkali metal hydroxide or a nitrogenous base, in whatever form it may exist in solution, with an organic solution of the enantiomeric mixture of 2-(6methoxy-2-naphthyl)propionic acid, hydrolyzable ester thereof, or combination of the foregoing, in which more than 82% but less than 99% thereof is in the S(+) enantiomeric form, in whatever form it may exist in solution, (ii) separating and recovering at least a portion of an aqueous phase of the resulting solution, (iii) feeding an acid into the recovered aqueous phase to form a reaction mass, and (iv) recovering from the reaction mass an enriched enantiomeric mixture of 2-(6-methoxy-2-naphthyl)propionic acid, hydrolyzable ester thereof, or combination of the foregoing.

Yet another embodiment of this invention is an enriched mixture of enantiomers of an optically active compound, the enriched mixture having a chiral purity of at least 99% in an enantiomeric form of the compound, the optically active compound having the formula:

$$R^1R^2R^3CCOOZ$$

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl groups, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is an alkali metal cation, a cation of a nitrogenous base or a combination of the foregoing, the enriched mixture being formed by a method which comprises the step of mixing an acid in whatever form it may exist in solution with an aqueous solution of a partially enriched mixture of enantiomers of the optically active compound, in whatever form the partially enriched mixture of enantiomers may exist in solution, to form a reaction mass comprising the enriched mixture.

FURTHER DESCRIPTION OF THE INVENTION

As will now be appreciated, an enantiomeric mixture of the optically active compound of this invention having a chiral purity in a first enantiomer of greater than 50% but less than 99% (partially enriched mixtures) is further enriched in the first enantiomer to a chiral purity level of at least 99% (and more preferably greater than 99%) by the process of this invention.

The optically active compound has the formula (I) above, where Z is an alkali metal cation (most preferably sodium or potassium) or a cation of a nitrogenous base such as a univalent amine cation (unmodified). As noted previously, the partially enriched mixture of enantiomers of the optically active compound may be formed from a process of this invention involving a partially enriched precursor mixture of enantiomers of a precursor optically active compound. This precursor optically active compound also has the formula (I), with the exception that Z is preferably a hydrogen atom, a $C_1$ to $C_6$ linear or branched alkyl group, or a combination thereof (modified). For all of the compounds of formula (I) (unmodified and modified), $R^1$, $R^2$, and $R^3$ are different and preferably are selected from among the following univalent groups: a hydrogen atom; $C_1$ to $C_6$ linear or branched alkyl (e.g., methyl or ethyl); $C_1$ to $C_6$ linear or branched haloalkyl (e.g., chloromethyl, fluoromethyl, chloroethyl, fluoroethyl, difluoromethyl, trifluoromethyl); aralkyl (e.g., benzyl, phenethyl); cycloalkyl (e.g., cyclopropyl, cyclobutyl, cyclopentyl, cyclohexyl); alkyl-substituted cycloalkyl (e.g., methylcyclohexyl, dimethylcyclopentyl); $C_6$ to $C_{18}$ aryl (e.g., phenyl, 1-naphthyl, 2-naphthyl, 2-biphenylyl, 3-biphenylyl, 4-biphenylyl, anthryl, fluoryl, tetrahydronaphthyl); alkyl-substituted aryl (e.g., tolyl, xylyl, trimethylphenyl, butylphenyl, and especially isobutylphenyl, 4-ethyl-1-naphthyl, 1,6-dimethyl-2-naphthyl, 4'-butyl-4-biphenylyl, 6-ethyl-2-biphenylyl); aryl substituted with $C_1$ to $C_4$ alkylthio, or $C_1$ to $C_4$ alkoxy, or cyano or halo, such as fluoro or chloro, especially fluoro-substituted biphenylyl groups; $C_1$ to $C_6$ linear or branched alkoxy (e.g., methoxy, ethoxy, propoxy, or butoxy); $C_6$ to $C_{18}$ aryloxy (e.g., phenoxy or phenoxy substituted with, for example, methyl, dimethyl, butyl or isobutyl, or phenoxy substituted with $C_1$ to $C_4$ alkylthio, or $C_1$ to $C_4$ alkoxy, or cyano or halo; $C_1$ to $C_6$ alkythio (e.g., methylthio, ethylthio); $C_3$ to $C_8$ cycloalkylthio; $C_6$ to $C_{18}$ arylthio; $C_6$ to $C_{18}$ arylcarbonyl (e.g., benzoyl); $C_4$ to $C_8$ cycloalkenyl (e.g., cyclopentenyl, cyclohexenyl); halo (e.g., fluoro or chloro); and $C_4$ to $C_{12}$ heteroaryl (e.g., furyl, pyrrolyl, thienyl).

One group of preferred compounds of the unmodified and modified forms of formula (I) are those in which $R^1$, $R^2$ and Z are as previously defined, and $R^3$ is a biphenylyl group (especially where one phenyl group is in the 4-position of the other phenyl group, i.e., a 4-biphenylyl or p-biphenylyl group) wherein either ring is, or both rings are, substituted by (i) $C_1$ to $C_4$ linear or branched alkyl, (ii) $C_1$ to $C_4$ linear or branched alkoxy, and/or (iii) halo.

Compounds of formula (I) (unmodified and modified) in which $R^1$, $R^2$ and Z are as previously defined, and $R^3$ is a naphthyl group (either 1-naphthyl or 2-naphthyl or both) wherein at least the ring (and most preferably the only ring) other than the ring to which the asymmetric carbon atom is bonded is substituted by (i) $C_1$ to $C_4$ linear or branched alkyl, (ii) $C_1$ to $C_4$ linear or branched alkoxy, and/or (iii) halo, is another group of preferred starting materials.

Still another group of preferred compounds of formula (I) (unmodified and modified) are those in which $R^1$, $R^2$ and Z are as previously defined, and $R^3$ is a phenyl group wherein the ring is substituted by (i) $C_1$ to $C_4$ linear or branched alkyl, (ii) $C_1$ to $C_4$ linear or branched alkoxy, and/or (iii) halo.

Compounds of formula (I) (unmodified and modified) wherein $R^1$, $R^2$ and Z are as previously defined, and $R^3$ is a phenyl group substituted by a $C_7$ to $C_{18}$ aryl group (especially a benzoyl group) constitutes yet another group of preferred starting materials.

As used in the process of this invention, the partially enriched mixture of the optically active compound of formula (I) is in aqueous solution. The aqueous solution of the partially enriched mixture of the optically active compound will typically have a concentration in the range of about 10 to about 50 wt % partially enriched mixture, more preferably in the range of about 20 to about 30 wt % partially enriched mixture.

The acid employed in the process of this invention may be virtually any inorganic or organic acid, with the proviso that the acid must have a pH which is lower than the pH of the acid form of the optically active compound. For reasons of cost and familiarity of use, sulfuric acid is preferred. The acid will typically be in dilute form. When sulfuric acid is used, the acid is preferably diluted to a concentration of about 15 to about 50 wt % sulfuric acid. When the partially enriched mixture of enantiomers of the optically active compound and/or the aqueous solution thereof is formed from the partially enriched precursor mixture of enantiomers of the precursor optically active compound, it is preferred that the amount of acid used in the process for enriching the chiral purity of the partially enriched mixture be less than 1 equivalent of acid per equivalent of optically active compound present in the aqueous solution.

In addition, when forming the partially enriched mixture of enantiomers and/or the aqueous solution thereof from a partially enriched precursor mixture of enantiomers of the precursor optically active compound, the base employed may be either an alkali metal hydroxide or a nitrogenous compound. The base may be introduced as part of an aqueous solution, although the base and water also may be introduced separately in any given order or simultaneously. The quantity of base employed can vary widely, and may depend upon the desired amount and quality of product. Once determined, that quantity is introduced into an organic solution of the partially enriched precursor mixture from which the partially enriched mixture of enantiomers of the optically active compound is formed. In effect, this process converts the precursor optically active compound(s) (carboxylic acid and/or ester) into the optically active compound(s) (i.e., carboxylic salt). Typically, the base in aqueous solution will be introduced at a concentration in the range of about 4 to about 15 wt %. The alkali metal hydroxide (or precursor thereof) in the form as introduced into the mixture to be subjected to chiral enrichment can be any alkali metal hydroxide or alkali metal oxide. The nitrogenous base can be ammonia, primary, secondary or tertiary, but is preferably a univalent amine cation. Preferred from the cost-effectiveness standpoint are sodium hydroxide, potassium hydroxide, sodium oxide, potassium oxide and any mixture or combination of these. When they are in the presence of water, the oxide is converted to hydroxide and ionization by the water will take place. Thus during the reaction the base is in whatever form into which it has been converted, if at all, as a natural consequence of being introduced into the system to be resolved. To avoid erroneous interpretations, let it be understood that the word "introduced" as used herein is not used in a limitive sense to mean that the base must be added to the mixture. Rather "introduced" is used in the ordinary sense to mean that the materials being used are brought together. How the materials are brought into the resolving mixture and whatever form they assume when in the mixture are both immaterial, so long as they get there to perform in accordance with this invention.

Any organic solvent which is inert to the other reactants in the process and is immiscible with water may be used as the diluent for the organic solution of the partially enriched precursor mixture of enantiomers. Non-limiting examples of suitable types of organic solvents include aromatic hydrocarbons, aliphatic hydrocarbons, chlorine-containing hydrocarbons, hydrocarbon amines, esters and ethers. Examples of such solvents include hexane, heptane, octane, benzene, toluene, xylene, chloroform, diethyl ether, ethyl acetate and the like. Ordinarily it is not necessary to introduce any other diluent or solvent. However if an ancillary diluent or solvent is employed it should be inert to the reactants and should not cause precipitation of the base introduced into the system.

When the partially enriched mixture of enantiomers is an enantiomeric mixture of a salt of 2-(6-methoxy-2-naphthyl) propionic acid and similar compounds, and this partially enriched mixture was formed from a precursor optically active compound in the form of 2-(6-methoxy-2-naphthyl) propionic acid, ester thereof, or a combination of the foregoing, the introduction of too much acid to the aqueous solution of the partially enriched mixture may prohibit the desired resolution to further enrich the mixture in the first enantiomer. Thus, when the precursor optically active compound is 2-(6-methoxy-2-naphthyl)propionic acid or other compounds of formula (I) above that may be negatively affected under the reaction conditions by exposure to excessive amounts of the acid, the effective amount of acid in the process is preferably less than 1 equivalent of acid per equivalent of optically active compound present in the aqueous solution. The amount of acid introduced to the aqueous solution of such partially enriched mixtures is more preferably in the range of about 0.7 to about 0.95 equivalent of acid per equivalent of base. Additionally, I have determined that a linear relationship may be expressed between the number of equivalents of acid per equivalents of base (Y) at or below which chiral resolution of 99% or greater is obtained, and the chiral purity (in %) of a partially enriched mixture of enantiomers of 2-(6-methoxy-2-naphthyl) propionic acid (X) having a chiral purity of 95% or greater but less than 99%, by the formula:

$$Y=0.10612X-9.4979$$

Thus, for example, if the partially enriched mixture of enantiomers has a chiral purity, X, of 96%, the maximum number of equivalents of acid per equivalent of base to be used to achieve a 99% chiral purity, Y, is 0.68962.

The process of this invention is conducted at a temperature in the range of about 25° C. to about 100° C., preferably in the range of about 80° C. to about 100° C., and most preferably in the range of about 92° C. to about 100° C. The optimum temperature conditions depend to some extent upon the particular optically active material being used in the chiral enrichment process. If necessary, this can readily be determined by conducting a few pilot experiments with the particular material or mixture to be enriched.

It is desirable to agitate the reaction mixture to ensure intimate contact among the components of the system. Preferably the process is conducted in a closed reaction vessel under autogenous pressure. Reaction times will generally vary inversely with reaction temperature, but should be selected to afford sufficient time for the reaction to proceed to the extent desired within the capabilities of the process under the set of circumstances involved. Typically, it will not be necessary to continue the reaction for any extended period of time after mixing the acid with the aqueous solution containing the partially enriched mixture of enantiomers.

Practice of this invention enables improvements in overall synthesis procedures which can be used for producing such finished end products as 2-(6-methoxy-2-naphthyl) propionic acid (also known as Naproxen), 2-(4-isobutylphenyl)propionic acid (also known as Ibuprofen), 2-(3-fluoro-4-biphenylyl)propionic acid (also known as Flurbiprofen), and 2-(3-benzoylphenyl)propionic acid (also known as Ketoprofen), for example.

The following examples serve to illustrate this invention, but do not limit it. All parts are by weight unless otherwise indicated.

EXAMPLE 1

A 943.08 gm solution of 14.85 wt % 2-(6-methoxy-2-naphthyl)propionic acid in toluene was charged to a 2000 mL round-bottom flask equipped with a stirrer. The stirred solution was heated to a temperature of 75–85° C. During a 10 minute period thereafter, an aqueous solution of NaOH (427.24 gm, 5.41 wt %) was slowly fed into the naproxen-toluene solution. The 2-liquid phase solution was then aged at 80° C. for 30 minutes and cooled to 40° C. over an additional 50 minute period. The phases then were allowed to separate by settling for 5 minutes. The aqueous phase (an aqueous solution of sodium naproxen) was recovered and determined to weight 562.31 gm, to contain 25.48 wt % sodium naproxen, and to have an S(+)-isomer purity of 98.15%.

A portion of this aqueous sodium naproxen solution (487.81 gm) was charged to a 1000 ml round-bottom flask, heated, and maintained at 80° C. Dilute sulfuric acid (73.55 gm, 29.61 wt % $HSO_4$) was fed into the solution slowly with a syringe pump over 196 minutes. The white slurry was aged at 80° C. for 2 hours. The free acid naproxen product was recovered by centrifugation, washed with 601.50 gm hot (80° C.) water, and dried in a vacuum oven. Weight of the free acid naproxen product was 103.37 gm, with a S(+)-isomer chiral purity of 99.31%.

EXAMPLE 2

A total of 920.48 gm of an aqueous solution of sodium naproxen, prepared in accordance with the procedure of Example 1 and having 24.04 wt % sodium naproxen and a S(+)-isomer chiral purity of 95.67%, is heated to and maintained at 80° C. To this solution, 23.52 gm of dilute (29.70 wt %) sulfuric acid was fed slowly over 51.5 minutes. The resulting slurry was aged at 80° C. for 30 minutes. A total of 69.05 gm of additional dilute (29.70 wt %) sulfuric acid was then fed into the slurry over an additional 157.5 minutes. The resulting slurry was agitated at 80° C. for 120 minutes. A portion of the resulting slurry was filtered, washed with 80° C. water, and dried under vacuum in an oven at 90° C. The resulting free acid naproxen product had a chiral purity of 99.05% in the S(+)-isomer form.

EXAMPLE 3

A total of 6029.3 gm of an aqueous solution of sodium naproxen, prepared in accordance with the procedure of Example 1 and having 19.05 wt % sodium naproxen and a S(+)-isomer chiral purity of 97.81%, is heated to and maintained at 92° C. To this solution, 665.73 gm of dilute (30.88 wt %) sulfuric acid was fed continuously over 95 minutes. The resulting slurry was aged at 89° C. for 30 minutes and cooled to 80° C. in 30 minutes. The product was isolated using a basket centrifuge, washed with 5837 gm of hot (80° C.) water, and dried under vacuum in an oven at 90° C. A total of 993.84 gm of dry free acid naproxen final product was obtained and determined to have a chiral purity of 99.03% in the S(+)-isomer form.

As can be seen from the foregoing, this invention provides a highly efficient method for producing an enantiomeric mixture of the optically active compound having chiral purity equal to or in excess of 99% in the enantiomer by which the starting mixture was partially enriched.

The entire disclosure of each and every U.S. patent referred to in any portion of this specification is incorporated herein by reference.

It is to be understood that the reactants and components referred to by chemical name or formula anywhere in the specification or claims hereof, whether referred to in the singular or plural, are identified as they exist prior to coming into contact with another substance referred to by chemical name or chemical type (e.g., another reactant, a solvent, or etc.). It matters not what chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, blended or mixed with one or more other substances, components and/or ingredients in accordance with the present disclosure. The fact that the substance, component or ingredient may have lost its original identity through a chemical reaction or transformation during the course of such contacting, blending or mixing operations is thus wholly immaterial for an accurate understanding and appreciation of this disclosure and the claims thereof.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A method for enriching the chiral purity of a partially enriched mixture of enantiomers of an optically active compound, a major portion of the partially enriched mixture of enantiomers comprising a first enantiomer of the optically active compound, a minor portion of the partially enriched mixture of enantiomers comprising a second enantiomer of the optically active compound, the optically active compound having the formula:

where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl groups, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is an alkali metal cation, a cation of a nitrogenous base or a combination of the foregoing, the method comprising:

mixing an acid in whatever form it may exist in solution with an aqueous solution of the partially enriched mixture of enantiomers, in whatever form the partially enriched mixture of enantiomers may exist in solution, to form a reaction mass comprising a further enriched mixture of enantiomers of the optically active compound, the further enriched mixture of enantiomers comprising a higher percentage of the first enantiomer than the partially enriched mixture.

2. A method according to claim 1 further comprising the step of recovering the further enriched mixture of enantiomers from the reaction mass.

3. A method according to claim 1 wherein Z is an alkali metal cation.

4. A method according to claim 1 wherein the acid is sulfuric acid.

5. A method according to claim 4 wherein the sulfuric acid has a concentration in the range of about 15 to about 50 wt % sulfuric acid.

6. A method according to claim 1 wherein $R^1$ is a hydrogen atom, $R^2$ is alkyl, and $R^3$ is alkylaryl, alkoxyaryl or haloaryl.

7. A method according to claim 1 wherein at least 99% of the further enriched mixture of enantiomers is comprised of the first enantiomer.

8. A method according to claim 1 wherein the partially enriched mixture of enantiomers and/or the aqueous solution thereof are formed by a process which comprises
(i) mixing (A) a base comprising an alkali metal hydroxide or a nitrogenous compound, and (B) water, or (C) an aqueous solution formed from (A) and (B), with an organic solution of a partially enriched precursor mixture of enantiomers of a precursor optically active compound, in whatever form the partially enriched precursor mixture may exist in solution, the precursor optically active compound having the formula:

$R^1R^2R^3CCOOZ$ where $R^1$, $R^2$, and $R^3$ are different from each other and are selected from the group consisting of a hydrogen atom, hydrocarbyl groups, hydrocarbyloxy groups, hydrocarbylthio groups, hydrocarbylcarbonyl groups, halohydrocarbyl groups, hydrocarbyloxyhydrocarbyl groups, heteroaromatic groups, and halogen atoms, with the proviso that none or only one of $R^1$, $R^2$, and $R^3$ can be a halogen atom, and where Z is a hydrogen atom, a hydrocarbyl group, or a combination of two or more of the foregoing, and
(ii) separating and recovering at least a portion of an aqueous phase of the resulting solution.

9. A method according to claim 8 wherein the base is an alkali metal hydroxide.

10. A method according to claim 9 wherein the alkali metal hydroxide is sodium hydroxide and/or potassium hydroxide.

11. A method according to claim 8 wherein the acid is sulfuric acid.

12. A method according to claim 11 wherein the sulfuric acid has a concentration in the range of about 15 to about 50 wt % sulfuric acid.

13. A method according to claim 8 wherein $R^1$ is a hydrogen atom, $R^2$ is alkyl, and $R^3$ is alkylaryl, alkoxyaryl or haloaryl.

14. A method according to claim 8 wherein at least 99% of the further enriched mixture of enantiomers is comprised of the first enantiomer.

15. A method according to claim 8 wherein the major portion is in the range of greater than 82% and less than 99%, and wherein the first enantiomer is the S(+) enantiomeric form.

16. A method according to claim 8 wherein in the formula for the optically active compound $R^1$ is a hydrogen atom, $R^2$ is alkyl, $R^3$ is alkylaryl, alkoxyaryl or haloaryl, and Z is a hydrogen atom; and wherein the base is sodium hydroxide and/or potassium hydroxide.

17. A method according to claim 8 wherein the ratio of (i) the acid to (ii) the optically active compound present in the aqueous solution of the partially enriched mixture of enantiomers, is less than one equivalent of acid per equivalent of optically active compound.

18. A method according to claim 17 wherein the first enantiomer is the S(+) enantiomeric form, and at least 99% of the further enriched mixture of enantiomers is comprised of the first enantiomer.

19. A method according to claim 18 wherein the major portion is in the range of greater than 82% and less than 99%.

20. A method according to claims 1 wherein the optically active compound is one or more salts of 2-(6-methoxy-2-naphthyl)propionic acid, the major portion is in the range of more than 82% and less than 99%, and the first enantiomer is the S(+) enantiomer.

21. A method according to claim 20 wherein the optically active compound is 2(6-methoxy-2-naphthyl)propionic acid sodium salt.

22. A method according to claim 20 wherein the acid is sulfuric acid.

23. A method according to claim 22 wherein the sulfuric acid has a concentration in the range of about 15 to about 50 wt % sulfuric acid.

24. A method according to claim 20 wherein the base is an alkali metal hydroxide.

25. A method according to claim 24 wherein the alkali metal hydroxide is sodium hydroxide and/or potassium hydroxide.

26. A method according to claim 20 wherein the further enriched mixture has a chiral purity of at least 99% in the S(+) enantiomeric form.

27. A method according to claim 8 wherein the precursor optically active compound is 2-(6-methoxy-2-naphthyl)propionic acid, hydrolyzable ester thereof, or combination of the foregoing, the major portion is in the range of more than 82% and less than 99%, and the first enantiomer is the S(+) enantiomer.

28. A method according to claim 27 wherein the ratio of (i) the acid to (ii) the optically active compound present in the aqueous solution of the partially enriched mixture of enantiomers, is less than one equivalent of acid per equivalent of optically active compound.

29. A method according to claim 27 wherein the further enriched mixture of enantiomers has a chiral purity of at least 99% in the S(+) enantiomeric form.

30. A method according to claim 28 wherein the acid is sulfuric acid.

31. A method according to claim 30 wherein the sulfuric acid has a concentration in the range of about 15 to about 50 wt % sulfuric acid.

32. A method according to claim 28 wherein the base is an alkali metal hydroxide.

33. A method according to claim 32 wherein the alkali metal hydroxide is sodium hydroxide and/or potassium hydroxide.

34. A method for enriching the chiral purity of an enantiomeric mixture of 2-(6methoxy-2-naphthyl)propionic acid, hydrolyzable ester thereof, or combination of the foregoing, which method comprises (i) mixing an aqueous solution of a base comprising an alkali metal hydroxide or a nitrogenous base, in whatever form it may exist in solution, with an organic solution of the enantiomeric mixture of 2-(6-methoxy-2-naphthyl)propionic acid, hydrolyzable ester thereof, or combination of the foregoing, in which more than 82% but less than 99% thereof is in the S(+) enantiomeric form, in whatever form it may exist in solution, (ii) separating and recovering at least a portion of an aqueous phase of the resulting solution, (iii) feeding an acid into the recovered aqueous phase to form a reaction mass, and (iv) recovering from the reaction mass an enriched enantiomeric mixture of 2-(6-methoxy-2-naphthyl)propionic acid, hydrolyzable ester thereof, or combination of the foregoing.

35. A method according to claim 34 wherein the ratio of (i) the acid to (ii) the optically active compound present in the recovered aqueous phase, is less than one equivalent of acid per equivalent of optically active compound.

* * * * *